Figure 1:
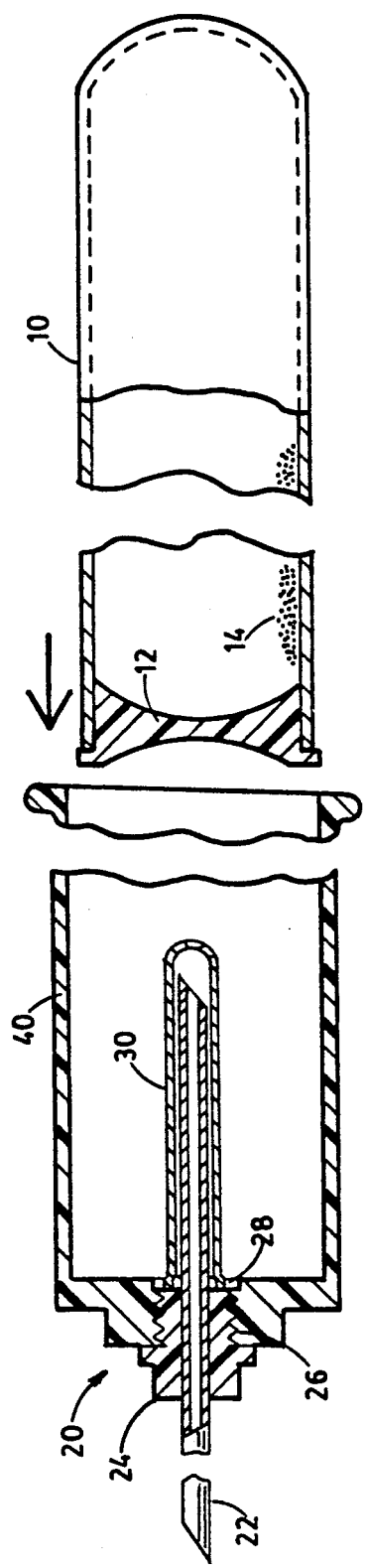

United States Patent [19]

Shanbrom

[11] Patent Number: 5,156,973
[45] Date of Patent: * Oct. 20, 1992

[54] ANTIVIRAL BLOOD SAMPLING PROCESS AND APPARATUS

[76] Inventor: Edward Shanbrom, 2252 Liane La., Santa Ana, Calif. 92705

[*] Notice: The portion of the term of this patent subsequent to Jul. 7, 2007 has been disclaimed.

[21] Appl. No.: 424,183

[22] Filed: Oct. 19, 1989

Related U.S. Application Data

[63] Continuation-in-part of Ser. No. 321,522, Mar. 9, 1989, abandoned, and a continuation-in-part of Ser. No. 290,161, Dec. 28, 1988, Pat. No. 4,891,221, and a continuation-in-part of Ser. No. 276,113, Nov. 23, 1988, abandoned.

[51] Int. Cl.$^5$ ............................................. G01N 31/00
[52] U.S. Cl. ......................................... 436/16; 435/2; 436/18
[58] Field of Search ...................... 514/570, 25; 435/2; 436/16, 18

[56] References Cited

PUBLICATIONS

Pompei et al.—Chem. Abst. vol. 93(1980) p. 19069W.
Pompei—Chem. Abst. vol. 92(1980) p. 104967M.

*Primary Examiner*—Sam Rosen
*Attorney, Agent, or Firm*—Grant L. Hubbard

[57] ABSTRACT

The treatment of blood or body fluid and body fluid samples to inactivate or destroy infective viruses, such as the cytomegalovirus, by mixing the sample with an effective amount of glycyrrhizic triterpenoid-detergent, glycyrrhizic triterpenoid-glycerol or glycyrrhizic triterpenoid-EDTA, combination followed by analysis or testing for diagnostic or other purposes is disclosed.

17 Claims, 1 Drawing Sheet

ANTIVIRAL BLOOD SAMPLING PROCESS AND APPARATUS

CROSS-REFERENCE TO RELATED APPLICATION

This is a continuation-in-part of U.S. Patent Applications Ser. No. 321,522, filed Mar. 9, 1989, now abandoned. Ser. No. 290,161, filed Dec. 28, 1988, now U.S. Pat. No. 4,891,221 and Ser No. 276,113, filed Nov. 23, 1988, now abandoned to which priority is claimed.

FIELD OF THE INVENTION

This invention relates to apparatus and methods for sampling blood and body fluids and the handling of resulting samples to prevent infection of doctors, nurses, medical technicians and other health care workers by sample-borne virus.

BACKGROUND OF THE INVENTION

This invention relates to the sampling of blood and body fluids to inactivate or destroy infective viruses.

Those who deal with blood and other invasively obtained body fluid samples risk infection from the samples. Those at risk include the doctor, nurse or clinical technician who takes the sample, the technicians who handle the sample and who use the sample in conducting analyses and tests, those who handle the sampling and testing equipment and apparatus, and the entire chain of individuals who attend to the disposal of sampling apparatus and the like, from the individuals who pick up the used apparatus through those who ultimately dispose of the apparatus, usually in specially designed high-temperature furnaces.

The risk is substantial, as evidenced by the fact that nearly all health care professionals with long experience carry the Epstein-Barr virus (EBV) and/or cytomegalovirus (CMV), the latter being probably the most ubiquitous of the pathogenic viruses. Other pathogenic viruses to which health care workers, and those who handle blood and fluid sampling and handling apparatus, are exposed include hepatitis and human immunodeficiency virus (HIV) as well as a large number of less life-threatening viruses.

CMV is frequently associated with *Pneumoncystis carinii* and may cause or contribute to encephalitis and colitis and may be associated with Kaposi's sarcoma in AIDS patients. CMV carriers frequently exhibit no symptoms of infection; however, the direct and contributory effects of CMV in infectious diseases is so pervasive and subtle that a CMV infection is to be presumed if another causative agent cannot be established.

CMV is a member of the human herpesvirus (HV) group, which are responsible for much of mankind's discomfort and pain. The herpesviruses represent a very large, clearly defined group of viruses which are responsible for, or involved in, cold sores, shingles, a venereal disease, mononucleosis, eye infections, birth defects and probably several cancers. Three subfamilies are of particular importance. The alpha subfamily includes HV-1 (herpes virus simplex 1) which causes cold sores, fever blisters, eye and brain infections, HV-2 (herpes virus simplex 2) which cause genital ulceration, and HV-3 (HV varicella zoster) which causes chicken pox, shingles and brain infections. The beta subfamily includes HV-5, the principal member of which is CMV discussed above. The gamma subfamily includes HV-4 (Epstein-Barr) which causes infectious mononucleosis and is involved in Burkitt's lymphoma and nasopharyngeal carcinoma. Additional possibly pathogenic herpes viruses no doubt exist, one type of which, HV-6, of unknown pathogenicity has been identified. (Niederman, J. C. et al., The Lancet, Oct. 8, 1988, 817.) There is evidence that the methods of this invention are effective in inhibiting the transmission of infections caused by many and perhaps all of the pathogenic herpes viruses.

At least one of the retroviridae is susceptible to the treatment of this invention, according to presently available data. The most notorious of the retroviridae, HIV-1, the only virus thus far identified as inducing AIDS in humans, is inactivated and/or killed using the methods and compositions of this invention. Other retroviridae are considered to be susceptible to the present invention. The enormity of the AIDS threat is so great as virtually to defy analysis. While the fear of HIV-caused AIDS is so pervasive in the United States and the more developed western world as to strike fear into all who are exposed to blood and other body fluids of a large number of individuals, the magnitude of the potential for disaster posed by HIV is, perhaps, better gauged by the fact that in central Africa and other third-world countries AIDS infects up to one-third of the population.

HIV antibody screening of blood and organ donors has become an important but routine step in preventing the infection of the donee patient, (see Wilhelmus, K. R. et al., *Ophthalmologica* (Switzerland) 1987, 195(2) 57; Mal'khanov, V. B. et al., *Vopr Virusol* 1987, 32(2) 21; Salisbury, J. D. et al., *Ophthalmic Surg* 1984, 15(5) 406; Beekhuis, W. H., *Doc Ophthalmol* 1983, 55(1-2) 31; Collin, H. B., *Arch Ophthalmol* 1976, 94(10) 1726), but the risk to those who treat a large number of individuals, some of whom are certain to carry HIV, remains a very serious problem indeed.

The addition of detergents to various blood fractions has been described. My European Patent Specification 0 050 061, published Dec. 11, 1985, in which the term "detergent" is equated with the term "amphophil" to encompass cationic, anionic and nonionic detergents, describes the addition of various detergents to plasma protein products and suggests the addition thereof to other blood derivative products to inactivate virus and for other purposes, followed by the removal of the detergent from the product. High concentrations of detergents, from 0.25 to 10%, were required the process described in the European patent specification.

Bosslet and Hilfenhause, European Patent Specification 0 278 487, discloses that high concentrations of selected detergents inactivate certain envelope viruses.

Neurath and Horowitz, e.g. U.S. Pat. Nos. 4,540,573, 4,481,189, and 4,591,505, indicate, however, that detergent alone is not effective as an antiviral agent in blood plasma and related products. In spite of these teachings, however, it seems safe to conclude that at least some classes of detergents in high concentrations in some types of blood derivatives do have some inactivating effect. The extent and efficacy of such procedures seems open to considerable doubt, however.

My copending patent application Ser. No. 07/321,522, filed Mar. 9, 1989, describes and claims a method for inactivating virus in blood samples using glycyrrhizic triterpenoid compounds.

The invention described and claimed herein is an improvement thereof and is based upon the discovery of unique synergistic improvement results when detergent, even trace amounts of detergent, are combined in the blood or blood product sample with glycyrrhizic triterpenoid compounds.

The invention described and claimed herein is an improvement thereof and is further based upon the discovery of unique synergistic improvement results when glycerol, even trace amounts of glycerol, are combined in the blood or blood product sample with glycyrrhizic triterpenoid compounds.

Further, the invention described and claimed herein is an improvement thereof and is further based upon the discovery of unique synergistic improvement results when glycerol, even trace amounts of ethylene diamine tetraacetic acid or salts thereof (EDTA), are combined in the blood or blood product sample with glycyrrhizic triterpenoid compounds.

SUMMARY OF THE INVENTION

The present invention is embodied in apparatus for taking blood samples and samples of other body fluids which comprise, as a part of the apparatus, one or more glycyrrhizic triterpenoid compounds in an amount of from 0.0001 to 10 wt/%, preferably about 0.1 to about 3 wt/%, and a detergent, preferably a nonionic detergent such as Tween ® and Triton X-100 ® in very low concentrations of from approximately 0.0001 to 5 wt/%, preferably 0.0001 to 0.01 wt/%, based on the size of the sample to be taken. There is a striking synergism between the detergent and the glycyrrhizic triterpenoid compound(s) rendering the combination surprisingly effective in inactivating susceptible viruses which may be in the sample.

The invention is also embodied in a method of taking or preparing blood and other body fluid samples for handling and for carrying out various analytical and diagnostic procedures and, ultimately, for disposal by mixing such samples with one or more glycyrrhizic triterpenoid compounds in a concentration of from 0.0001 to 10.0 wt/%, preferable from 0.1 to 3 wt/%, and from approximately 0.0001 to 5 wt/%, preferably 0.0001 to 0.01 wt/% of Tween ® or Triton X-100 ®, or other suitable detergent, based on sample size, sufficient to substantially inactivate susceptible viruses. Higher levels of detergent are also effective, but interference with diagnostic tests may result if the concentration of detergent is too high.

It is significant to note that the concentration levels of detergent which are suitable in this invention have little antiviral effect but when used in combination with glycyrrhizic triterpenoid compounds, increases the antiviral effectiveness very dramatically, resulting in as much as 1 to 3 logs higher inactivation than result with the same concentration of the glycyrrhizic triterpenoid compounds alone at the same concentration.

Thus, the present invention comprises methods for inactivating viruses in blood and other body fluids by the use of extracts of the well-known flavoring agent licorice, referred to here as glycyrrhizic triterpenoids or GTPD compounds in combination with acceptable amounts of detergent.

This invention is embodied in methods comprising treating blood and other body fluid samples with GTPD compounds, e.g. glycyrrhizic acid, its analogues such as carbenoxolone and cicloxolone, analogues thereof and the salts, esters and other derivatives thereof in combination with suitable detergent and thereafter conducting analyses and tests on the blood or fluid for diagnostic or other purposes.

The present invention is also embodied in apparatus for taking blood samples and samples of other body fluids which comprise, as a part of the apparatus, one or more glycyrrhizic triterpenoid compounds in an amount of from 0.0001 to 10 wt/% preferably about 0.1 to about 3 wt/%, and glycerol in very low concentrations of from approximately 0.0001 wt/% to 5 wt/%, preferably 0.0001 to 0.01 wt/%, based on the size of the sample to be taken. There is a striking synergism between the glycerol and the glycyrrhizic triterpenoid compound(s) rendering the combination surprisingly effective in inactivating susceptible viruses which may be in the sample.

The invention is also embodied in a method of taking or preparing blood and other body fluid samples for handling and for carrying out various analytical and diagnostic procedures and, ultimately, for disposal by mixing such samples with one or more glycyrrhizic triterpenoid compounds in a concentration of from 0.0001 to 10.0 wt/%, preferable from 0.1 to 3 wt/%, and from approximately 0.0001 to 5 wt/%, preferably 0.0001 to 0.01 wt/% of glycerol, based on sample size, sufficient to substantially inactivate susceptible viruses. Higher levels of glycerol are also effective, but interference with diagnostic tests may result if the concentration of glycerol is too high.

It is significant to note that the concentration levels of glycerol which are suitable in this invention have little antiviral effect but when used in combination with glycyrrhizic triterpenoid compounds increases the antiviral effectiveness very dramatically, resulting in as much as 1 to 3 logs higher inactivation than result with the same concentration of the glycyrrhizic triterpenoid compounds alone at the same concentration.

Thus, the present invention comprises methods for inactivating viruses in blood and other body fluids by the use of extracts of the well-known flavoring agent licorice, referred to here as glycyrrhizic triterpenoids or GTPD compounds in combination with acceptable amounts of glycerol.

The present invention is also embodied in apparatus for taking blood samples and samples of other body fluids which comprise, as a part of the apparatus, one or more glycyrrhizic triterpenoid compounds in an amount of from 0.0001 to 10 wt/%, preferably about 0.1 to about 3 wt/%, and EDTA in very low concentrations of from approximately 0.0001 to 5 wt/%, preferably 0.0001 to 0.01 wt/%, based on the size of the sample to be taken. There is a striking synergism between the EDTA and the glycyrrhizic triterpenoid compound(s) rendering the combination surprisingly effective in inactivating susceptible viruses which may be in the sample.

The invention is also embodied in a method of taking or preparing blood and other body fluid samples for handling and for carrying out various analytical and diagnostic procedures and, ultimately, for disposal by mixing such samples with one or more glycyrrhizic triterpenoid compounds in a concentration of from 0.0001 to 10.0 wt/%, preferable from 0.1 to 3 wt/%, and from approximately 0.0001 to 5 wt/%, preferably 0.0001 to 0.01 wt/% of EDTA, based on sample size, sufficient to substantially inactivate susceptible viruses. Higher levels of EDTA are also effective, but interference with diagnostic tests may result if the concentration of EDTA is too high.

It is significant to note that the concentration levels of EDTA which are suitable in this invention have little antiviral effect but when used in combination with glycyrrhizic triterpenoid compounds increases the antiviral effectiveness very dramatically, resulting in as much as 1 to 3 logs higher inactivation than result with the same concentration of the glycyrrhizic triterpenoid compounds alone at the same concentration.

Thus, the present invention comprises methods for inactivating viruses in blood and other body fluids by the use of extracts of the well-known flavoring agent licorice, referred to here as glycyrrhizic triterpenoids or GTPD compounds in combination with acceptable amounts of EDTA.

This invention is also embodied in methods comprising treating blood and other body fluid samples with GTPD compounds, e.g. glycyrrhizic acid, its analogues such as carbenoxolone and cicloxolone, analogues thereof and the salts, esters and other derivatives thereof in combination with suitable EDTA and thereafter conducting analyses and tests on the blood or fluid for diagnostic or other purposes.

This invention is, in one preferred embodiment, also embodied in any of the several types of devices known in the industry as "vacuum tubes" which comprise an invasive needle which is inserted into the vein, or other fluid-containing body structure, a test tube for collecting the sample, and a syringe-like sealing device for causing a vacuum to form inside the test tube when the test tube is moved relative to the sealing device. The interior of the test tube is in fluid communication, through the needle, with the vein or fluid-containing body structure, thereby causing the blood or fluid to flow into the test tube for further handling and testing. According to this invention, the test tube contains a predetermined amount of a GTPD compound, which consists essentially of glycyrrhizin, carbenoxolone, cicloxolone analogues and derivatives thereof, or mixtures thereof in combination with detergent, the amount being effective to inactivate HIV and/or other susceptible viruses. The GTPD compound may also serve as an anticoagulant, alone, or in mixture with other anticoagulants. The sample is shaken or otherwise manipulated to assure mixing of the GTPD compounds. Within a short time, as short as a very few minutes, using appropriate concentrations, the susceptible pathogenic viruses in the sample are inactivated and the risk of infection therefrom no longer exists.

Thus, the invention relates to methods for collecting and treating blood and fluid samples with GTPD compounds, e.g. glycyrrhizic acid, its analogues such as carbenoxolone and cicloxolone, analogues thereof and the salts, esters and other derivatives thereof in combination with detergent, and to blood plasma for transfusion containing such compounds which is free of HIV virus capable of infecting the donee of such plasma. Inactivation of other viruses to a greater or lesser extent also results. Alternatively, the glycyrrhizic triterpenoid compound-detergent synergistic combination may be added to the sample after collection of the sample, which with reduction or elimination of the risk of infection of workers who handle the blood and products thereof is greatly reduced.

BRIEF DESCRIPTION OF THE DRAWING

FIG. 1 is a side view, in partial cut-away and cross-section, depicting a vacuum tube sampling apparatus modified according to this invention to introduce the blood sample into a vacuum tube which contains virus-inactivating composition.

FIG. 2 is a side view, in partial cut-away and cross-section, depicting apparatus for introducing liquid virus-inactivating composition into the vacuum tube before taking the blood sample.

DESCRIPTION OF THE PREFERRED EMBODIMENT

Glycyrrhizic acid, 2O-β-carboxy-11-oxo-3O-norolean-12-en-3β-yl-2-O-β-D-glucopyranuronsyl-α-D-glucopyranosiduronic acid, glycyrrhizinic acid or glycyrrhetinic acid glycoside and glycyrrhizin (also referred to as biosone, enoxolone, and glycyrrhetin), are extracts from Glycyrrhiza, better known as licorice, an extract of the dried rhizome and roots of Glycyrrhiza glabra. Glycyrrhizin is a triterpene and is exemplary of the triterpenes to which this invention relates. Analogous triterpenes to which this invention relates include carbenoxolone and cicloxolone. This invention thus relates to glycyrrhizic acid and analogues thereof, in the form of acids, salts, esters and other derivatives. Many such derivatives are known, such as, for example: Glycyrrhisoflavone; Benzyl glycyrrhetinate; Glycyrrhizinic acid ammonium salt; Glycyrrhizinic acid hydrolase; Glycyrrhizinic acid; Zinc glycyrrhizinate; Glycyrrhetic acid 3-O-(hydrogen sulfate); Glycyrrhetinyl stearate; Monopotassium glycyrrhetin; 3-Oxo-18-α-glycyrrhetinic acid; 11-Deoxoglycyrrhetinic acid hydrogen maleate sodium salt; 11-Deoxoglycyrrhetinic acid hydrogen maleate; 18-α-Glycyrrhizic acid diammonium salt; Monoarginine glycyrrhizinate; Potassium glycyrrhizinate; 18-α-Glycyrrhizinic acid; 18-α-Glycyrrhizic acid monosodium salt; 18-α-Glycyrrhizic acid dipotassium salt; 18-α-Glycyrrhizic acid disodium salt; 18-α-Glycyrrhizic acid monopotassium salt; Glycyrrhizinic acid mono-triethanolamine) salt; Glycyrrhizinic acid disodium salt; Trisodium glycyrrhizinate; Dipotassium glycyrrhizate; Triammonium glycyrrhizinate; Dioxoglycyrrhetinic acid; Sodium glycyrrhizate; Ammonium glycyrrhizinate; Tripotassium glycyrrhizate; Glycyrrhetinic acid nicotinate morpholine salt; Benzyl 3-O-benzyl-18-β-glycyrrhetate; 3-O-Acetylglycyrrhetaldehyde; Glycyrrhizic acid monopotassium salt; Magnesium di-3-acetyl-18-β-glycyrrhetinate; Magnesium monomethoxymono-3-acetyl-18-β-glycyrrhetinate; Dehydrocorydaline glycyrrhizate; Ruscogenin acetylglycyrrhetinate; Glycyrrhetic acid 3-O-glucuronide; Cinoxolone; crotyl glycyrrhetate; Glycyrrhizin trimethyl ester; 3-O-Acetylglycyrrhetoyl chloride; Aluminum acetylglycyrrhetate; Dipotassium glycyrrhetinate; Methyl 11-deoxo-18-a-glycyrrhetate; Calcium potassium glycyrrhizinate; Glycyrrhetic acid monophosphate; β-glycyrrhetinicacid 3-acetate; 24-Hydroxyglycyrrhetic acid; 3-O-Acetyl-18-β-glycyrrhetamide; Deoxyglycyrrhetic acid; N-(18-β-Glycyrrhetyl)glycine; 3-O-Propionyl-18-β-glycyrrhetic acid; o-(18-β-Glycyrrhetamido)benzoic acid; Glycyrrhetol; Stearyl glycyrrhetinate; Glycyrrhizic acid monosodium salt; Methyl 3-O-acetylglycyrrhetinate; Carbenoxolone sodium; Ammonium glycyrrhetinate; 3-Dehydro-18-β-glycyrrhetic acid; 3-O-Acetyl-18-β-glycyrrhetic acid; Methyl 3-O-toxylglycyrrhetate; Biogastrone; Glycyrrhetinic acid phthalate; Lauroyl glycyrrhetinate; Methyl 3-oxoglycyrrhetate; Methyl-β-glycyrrhetinate; Sodium glycyrrhetinate; Methyl glycyrrhetate; 18-α-Glycyrrhetic acid; Glycyrrhizin; 11-Deoxo-18-β-glycyrrhetic acid; Glycyrrhetic acid; Carbenoxolone sodium; Biogastrone; Glycyrrhizin and the virucidal analogues and derivatives thereof are referred to for convenience herein as glycyrrhizic triterpenoids abbreviated GTPD.

In addition to its use as a flavoring agent, licorice has long been a common folk medicine for the treatment of sore throats. While not widely known, various extracts of and preparations derived from licorice, e.g. glycyrrhizin and its derivatives, principally the salts of glycyrrhizic acid, have also been used to a limited degree for many years as an orally administered medication for the treatment of peptic ulcers (Chandler, R.F., *Can. Pharm. J.*, V118, No. 9, 1985), and oral administration of glycyrrhizin contemporaneously with saponin antiinflamatory agents has been reported to inhibit saponin and saponigen hemolysis (Segal, R. et al., *Biochem. Pharmacol.* 26, 7 1977).

Inactivation of viruses, in vitro, under certain conditions, has been reported (see, e.g., Pompei, R., *Expri-entia* (Switzerland) 36/3 1980). Such anti-viral activity as GTPD compounds sometimes exhibit has been attributed to reverse transcriptase-inhibitory activity (Nakashima, H. et al., *Jpn. J. Cancer.* Res. 78,8 1987) and to enhancement of interferon-gamma production (Shinada, M. et al., *Proc. Soc. Exp. Biol.* 181,2 1986), but the exact mechanism of the anti-viral function has not been confirmed.

Dargan, D. J., and Subak-Sharpe, J. H., (J. Gen. Virol., 1985–1986) reported antiviral action of carbenoxolone and cicloxolone on herpes simplex virus. Their dose-response experiments showed cicloxolone sodium or carbenoxolone sodium interfered with the HSV replication cycle and reduced the infectious virus yield by 10,000- to 100,000-fold, cicloxolone being the more potent anti-herpes agent, but no consistent effect on HSV DNA synthesis was identified. Some inhibition of cellular DNA synthesis was observed, but this was relatively slight.

Csonka, G. W., and Tyrrel, D. A., (*Br. J. Vener. Dis.* 1984, 60 (3) p178) undertook a double blind clinical study to compare the efficacy of carbenoxolone and cicloxolone creams with placebo in initial and recurrent herpes genitalis and reported significant differences in the time to disappearance of pain and the healing of lesions using cicloxolone, but carbenoxolone showed insignificant beneficial effect.

GTPDs have also been evaluated therapeutically as anti-viral agents in the chemotherapy of acquired immune deficiency syndrome (AIDS) (Ito, M., Yamamoto, N., *Yakaguaku Zasshi* (Japan) 188,2 1988), treatment of Epstein-Barr virus (EBV) infections (Van Benschoten M. M., *Am. J. Acupunct*, 16,1 1988), and in the treatment of chronic hepatitis (Fujisawa, K. et al., *Asian Med. J.* (Japan), 23,10 1980).

The anti-viral activity of GTPDs varies so unpredictably as to preclude any generalized statements as to whether such compounds have general anti-viral effect or even as to whether such compounds will generally have anti-viral value as to any given virus. While GTPD drugs do, in some environments and under some conditions, exhibit some activity against some viruses, no anti-viral therapy based on GTPDs or in vitro anti-viral application of GTPDs has been generally accepted. It has been clearly demonstrated that vesicular stomatitis virus, one of the rhabdoviruses which has an envelope of glycoprotein, matrix protein and lipid, is inactivated. There is reason to believe that the GTPD compounds attack the lipid component of the virus envelope, but the nature of the attack on viruses has not been defined sufficiently to permit an accurate and specific categorization of the types and classes of viruses against which the GTPD compounds are effective. It is believed that the GTPD compounds have some reactivity with and/or solubility in lipids and/or lipoproteins; however, these compounds are not properly considered as surfactants or detergents because red blood cells are not only not lysed, in low concentrations of GTPD compounds, but appear to be stabilized, and lipids are not dissolved. There is evidence that the GTPD compounds attach to the lipid-containing cell walls, viral envelopes, etc. and may penetrate the envelope, but it would be premature to postulate a precise mechanism of action of the GTPD compounds on a cellular basis at the present time.

The AIDS-causing viruses, HIV-I and HIV-II, are the first retroviruses identified as pathogenic in man. While HIV are more fragile than most infectious viruses and are susceptible to destruction by most virus-inactivating methods, such as heating, use of strong detergent compounds, etc., these methods also damage cells, e.g. the red blood cells, and, therefore, are not suitable for use in treating blood samples. It has now been discovered that glycyrrhizin, carbenoxolone and cicloxolone and the analogues thereof not only inactive HIV in blood but, in some instances, also serve as effective anticoagulants and do not interfere with standard blood analyses.

One of the preferred method of carrying out the invention comprises providing a pre-packaged vacuum-tube-type sampling device which contains an amount of the GTPD compound, either in solution or in dry form, e.g. glycyrrhizin, carbenoxolone or cicloxolone, to comprise from about 0.005 to about 10 wt/%, generally in the range of about 0.1 to about 3 wt/%, of the sample in combination with from approximately 0.0001 to 5 wt/%, preferably 0.0001 to 0.01 wt/% of a detergent, sufficient to inactivate CMV and/or other viruses in blood sample. If the GTPD is to be used as the sole anticoagulant, a quantity sufficient to result in at least about 2 wt/% of the collected blood should be in the collection container. The collected blood is held for a sufficient period of time, e.g. 15 minutes or more at normal room temperatures or for an hour or more at near 0° C., to assure that the virus is inactivated. (See, also, other patents which disclose various detergent-blood component combinations or processes, e.g. Canada 1,158,997, Dec. 20, 1983; U.S. Pat. No. 4,314,997, Feb. 9, 1982; U.S. Pat. No. 4,305,871, Dec. 15, 1981; U.S. Pat. No. 4,105,218, Apr. 25, 1978; U.S. Pat. No. 4,137,223, Jan. 30, 1979; U.S. Pat. No. 4,069,216, Jan. 17, 1989; and various publications, e.g. Johnson, A. J., MacDonald, V. E., Brind, J., *Vox Sang.* 36: 71–76 (1979). Many other patents and publications disclosing the use of detergents in connection with blood components or derivatives are known to exist, but none have been identified as being more relevant than those listed above.)

In carrying out this method, conventional blood collection containers are preferably used; however, the manner of collection is of no consequence vis-a-vis the effectiveness of this invention. Importantly, the analyses and tests on the samples are carried out without modification or adaptation.

The GTPD compounds of this invention may be added to conventional anticoagulants, e.g. citrate dextrose, citrate phosphate dextrose, EDTA, heparin, etc., to enhance the anticoagulant effect of these, or to replace, in whole or in part, such anticoagulants.

It has been established that an exemplary triterpenoid compound, carbenoxolone and cicloxolone, as well as glycyrrhizic acid and derivatives thereof, typically in the form of salts, in a concentration range of from about 0.005 to 10 wt/% when combined with detergent in the range of from 0.0001 to 5 wt/%, preferably under about 0.01 wt/%, greatly accelerates the inactivation of virus and increases the ultimate inactivation, typically by at least 1 log and as high as 3 logs.

Solutions of glycyrrhizic compounds in the range of from about 0.1 to about 2 or 3 wt,'% are presently considered optimal as to concentration, lower concentrations of glycyrrhizic compounds being possible when combined with detergent.

The full scope of types of detergents which may be used in this invention has not been fully determined. The essential requirements are that the detergent have a high detergency action and not interfere with the laboratory tests, at the level of addition involved.

The preferred detergents are classed as nonionic detergents, examples of which include: polyoxyethylene-based detergents such as TWEEN ® and octyl phenoxy polyethoxy ethanol-based detergents such as TRITON X-100 ®, which are preferred, and detergents based upon polyethylene glycol and condensation polymers of ethylene oxide and propylene glycol. These are, of course, merely examples of some of the more common classes of detergents suitable for use in this invention and other classes of nonionic detergents may be used.

Ionic detergents such as, for example, sodium lauryl sulfonates, may also be used, but it may be necessary to make adjustments in the laboratory procedures or results to compensate for the addition of components of the detergent.

A comparison of results using GTPD compounds alone, as described and exemplified in my copending application Ser. No. 321,522, filed Mar. 9, 1989, modified by adding from approximately 0.0001 to 5 wt/%, preferably 0.0001 to 0.01 wt/% detergent simply to keep the blood samples as free of additives as is possible and yet accomplish virus inactivation, two results were striking. First, inactivation adequate for most purposes, e.g. 2-4 log kills, could be obtained in a fraction of the time previously required. Secondly, the ultimate inactivation was increased by a minimum of 1 log in most cases and typically up to 3 logs, or more, in some instances.

The result was particularly surprising in view of the general lore of the art that low levels of detergent have little or inadequate anti-viral effects. Quite clearly, there is more here than a mere additive effect, since the GTPD effect plus a negligible or zero effect would have been predicted. It is speculated that in some way the detergent renders the cell membrane more accessible to GTPD, which is believed to attach to the membrane but which as no detergency of consequence. This is, however, only a speculation, and there is no hard evidence to support an elucidation of the mechanism of action.

The speed of action and ultimate inactivation achievable using GTPD alone or with detergent is also significantly increased by maintaining the blood at approximately body temperature, 27° C. or higher, up to 40°-45° C. with nearly any blood or blood derivative and up to 60° C. for certain heat-resistant derivatives.

Unlike the prior art, it is not necessary to remove the detergent. This feature, alone, is of very significant economic and practical importance.

Of the readily available GTPD compounds, carbenoxolone is preferred for its anti-viral effectiveness. The acid form of the GTPD compounds is only slightly soluble in water but is quite soluble in dimethyl sulfoxide. The salt, e.g. ammonium, sodium or potassium salts, of the GTPD compounds are, generally, soluble in water, the sodium and potassium salts being more soluble than the ammonium salts. It is, thus, convenient to purchase or prepare the GTPD compounds as sodium or potassium salts.

As reported in my aforesaid pending patent applications, the addition of the GTPD compound(s) to whole blood tends to stabilize erythrocytes against lysing and other damage, thus permitting testing and analysis, including blood cell counts and analysis.

This discovery is considered to be of potentially great importance. It is known that detergents tend to lyse cells, e.g. red blood cells, and that the presence of detergent in a concentration which is effective within a few hours to inactivate virus, to the extent such action occurs, severely damages the red blood cells and probably other cells of the blood. There is a second synergistic effect involved in the use of GTPD combined with detergent in that the net effect is to stabilize the cells rather than to tend to lyse the cells as would have been predicted from the prior art.

It has also been discovered that blood treated as described above, when fractionated to produce plasma, clarifies the plasma, eliminating the translucence characteristic of most plasma. Further, standard blood analysis, e.g. serum protein electrophoresis, basic blood chemistry tests, and lipid tests were unaffected by the presence of the GTPD additives of this invention. Thus, according to this invention, by a one-step addition of one or more GTPD compounds to whole blood at or after the time of collection (if a suitable anti-coagulant is used), the red blood cells are not only not lysed, but appear to be stabilized, CMV and other blood-borne viruses, e.g. HIV, are killed or inactivated, plasma is clarified, coagulation is inhibited, and conventional blood analysis are not significantly effected.

It has been established that the exemplary GTPD compounds glycyrrhizin, carbenoxolone and cicloxolone added to a concentration of 1 wt/% effectively reduces the CMV content by at least 1 log, carbenoxolone being about 100 times as effective at the 1 wt/% concentration as the other exemplary GTPD compounds. When the concentration of GTPD compound is increased to 2 wt/%, glycyrrhizin and cicloxolone each exhibited good anti-coagulant effect, sufficient to permit the omission of any other anticoagulant in most instances, while the limited anti-coagulant effect of carbenoxolone was insufficient. In both instances, however, a one, two or more log CMV inactivation was achieved. In a comparable evaluation, a >3 log kill of HIV was achieved using a 1 wt/% carbenoxolone treatment. A >4-6 log or greater kill can be achieved by the addition of from approximately 0.0001 to 5 wt/%, preferably 0.0001 to 0.01 wt/% of a detergent in accordance with this invention.

Thus, as a method of collecting whole blood, the invention is embodied in a process comprising introducing said blood into a transfusion blood container containing glycyrrhizic triterpenoid compound sufficient to comprise from 0.0001 to 10 wt/%, preferably from about 0.1 to about 3 wt/% of the total sample collected in combination to from 0.0001 to 5, preferably 0.0001 to 0.01 wt/% of a compatible detergent.

One of the preferred method of carrying out the invention comprises providing a pre-packaged vacuum tube type sampling device which contains an amount of the GTPD compound, either in solution or in dry form, e.g. glycyrrhizin, carbenoxolone or cicloxolone to comprise from about 0.005 to about 10 wt/%, generally in the range of about 0.1 to about 3 wt/%, of the sample in combination with from approximately 0.0001 to 5 wt/%, preferably 0.0001 to 0.01 wt/% of a glycerol, sufficient to inactivate CMV and/or other viruses in blood sample. If the GTPD is to be used as the sole anticoagulant, a quantity sufficient to result in at least about 2 wt/% of the collected blood should be in the collection container. The collected blood is held for a sufficient period of time, e.g. 15 minutes or more at normal room temperatures or for an hour or more at near 0° C., to assure that the virus is inactivated.

One of the preferred method of carrying out the invention comprises providing a pre-packaged vacuum-tube-type sampling device which contains an amount of the GTPD compound, either in solution or in dry form, e.g. glycyrrhizin, carbenoxolone or cicloxolone to comprise from about 0.005 to about 10 wt/%, generally in the range of about 0.1 to about 3 wt/%, of the sample in combination with from approximately 0.0001 to 5 wt/%, preferably 0.0001 to 0.01 wt/% of a EDTA, sufficient to inactivate CMV and/or other viruses in blood sample. If the GTPD is to be used as the sole anticoagulant, a quantity sufficient to result in at least about 2 wt/% of the collected blood should be in the collection container. The collected blood is held for a sufficient period of time, e.g. 15 minutes or more at normal room temperatures or for an hour or more at near 0° C., to assure that the virus is inactivated.

FIG. 1 depicts a vacuum tube blood sampling apparatus modified to embody the present invention. The vacuum tube 10 is provided with a sealing septum 12 which maintains a vacuum in the tube, as is conventional and well known. According to this invention, however, GTPD-detergent virus inactivating reagent mixture is also included in the vacuum tube as indicated at 14. In this embodiment, the GTPD virus inactivating compound is depicted as a powder which will dissolve in the blood sample; however, the compound may be in solution as will be described hereinafter. This invention is, thus embodied in a sampling vacuum tube which comprises a chamber for receiving the blood, a septum for receiving and sealing around a needle, the septum sealing the chamber and maintaining the chamber under a reduced pressure, i.e. vacuum, and virus-inactivating compound in the chamber.

The vacuum tube modified to embody the invention as described is used in conventional manner. For example, the needle assembly 20, which is conventionally received in sleeves protecting ends of the needle 22 maintaining sterility and protecting the user from injury, is screwed into the holder cylinder 40, the threaded portion on sleeve 24 being threadably received in the internally threaded passage 26 in the holder 40. The vacuum tube is moved, as shown by the arrow, such that the septum 12 receives, is punctured by and seals around the needle 22, pushing the resilient sleeve 30 off the end of the needle. This operation, which is conventional, is done after the distal end of the needle 22, shown at the left in the figures, is inserted in the patient's blood vessel. The vacuum in the tube draws the sample of blood and the vacuum tube is removed, allowing the sleeve 30 to re-cover the proximal end of needle 22. This may be repeated with as many vacuum tubes as desired for multiple sampling.

This operation is carried out using the vacuum tube of this invention in the conventional manner after which the blood sample is thoroughly mixed with the virus-inactivating composition in the sampling tube to assure intimate mixing of the blood and the virus-inactivating composition.

Figure 2:
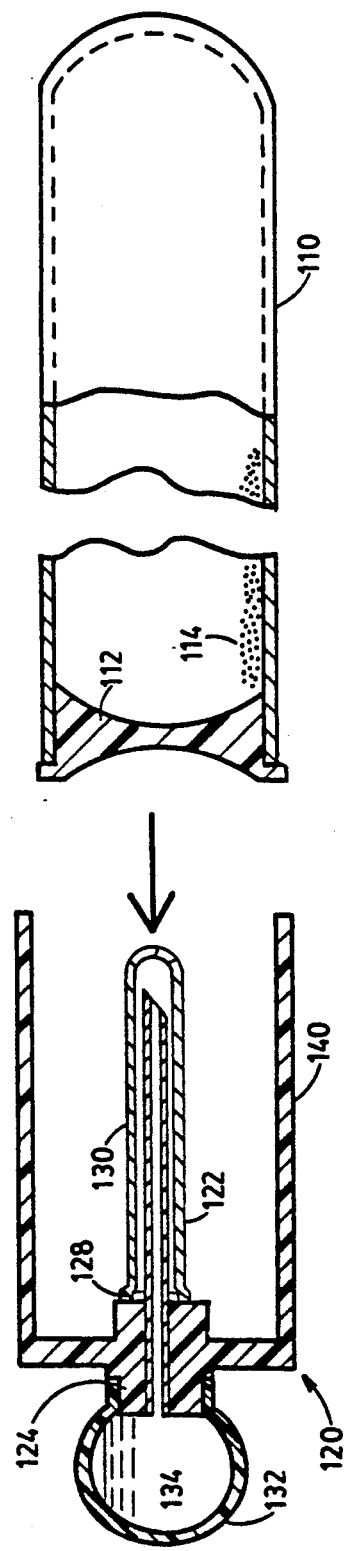

The virus-inactivating composition may be stored under vacuum in the vacuum tube and mixed directly with the blood, or it may be dissolved in water or buffer, which may, as indicated above, include other blood reagents, before sampling the blood. An exemplary apparatus for carrying out this variation in the invention is depicted in FIG. 2, wherein the vacuum tube 110, 112, 114 is as described. In this instance, the vacuum tube is inserted into a charging device 120 which comprises a needle 122 covered by a sheath 130 held on a shoulder 128 by the resilience of the sheath or by adhesive or fastener, moving the sheath 130 to the left as depicted and allowing the liquid 134 which is stored, in this exemplary embodiment, in a resilient or flexible pouch 132. The liquid may be pre-mixed reagent consisting essentially of a solution of GTPD-detergent composition alone or with buffering agents and other reagents which do not interfere with the action of the GTPD compounds, or it may be water or buffer solution which dissolves the reagent in the vacuum tube. In either instance, a vacuum tube which has therein a liquid which consists essentially of the virus inactivating composition is provided and used as described above.

Solutions of glycyrrhizic compounds in the range of from about 0.1 to about 2 or 3 wt/% are presently considered optimal as to concentration, lower concentrations of glycyrrhizic compounds being possible when combined with glycerol.

A comparison of results using GTPD compounds alone, as described and exemplified in my copending application Ser. No. 321,522, filed Mar. 9, 1989, modified by adding from approximately 0.0001 to 5 wt/%, preferably 0.0001 to 0.01 wt/% glycerol simply to keep the blood samples as free of additives as is possible and yet accomplish virus inactivation, two results were striking. First, inactivation adequate for most purposes, e.g. 2-4 log kills, could be obtained in a fraction of the time previously required. Secondly, the ultimate inactivation was increased by a minimum of 1 log in most cases and typically up to 3 logs, or more, in some instances.

The result was particularly surprising in view of the general lore of the art that low levels of glycerol have little or inadequate anti-viral effects. Quite clearly, there is more here than a mere additive effect, since the GTPD effect plus a negligible or zero effect would have been predicted. It is speculated that in some way the glycerol renders the cell membrane more accessible to GTPD, which is believed to attach to the membrane but which as no detergency of consequence. This is, however, only a speculation and there is no hard evidence to support an elucidation of the mechanism of action.

Solutions of glycyrrhizic compounds in the range of from about 0.1 to about 2 or 3 wt/% are presently considered optimal as to concentration, lower concentrations of glycyrrhizic compounds being possible when combined with EDTA.

A comparison of results using GTPD compounds alone, as described and exemplified in my copending application Ser. No. 321,522, filed Mar. 9, 1989, modified by adding from approximately 0.0001 to 5 wt/%, preferably 0.0001 to 0.01 wt/% EDTA simply to keep the blood samples as free of additives as is possible and yet accomplish virus inactivation, two results were striking. First, inactivation adequate for most purposes, e.g. 2–4 log kills, could be obtained in a fraction of the time previously required. Secondly, the ultimate inactivation was increased by a minimum of 1 log in most cases and typically up to 3 logs, or more, in some instances.

Quite clearly, there is more here than a mere additive effect. It is speculated that in some way the EDTA renders the cell membrane more accessible to GTPD, which is believed to attach to the membrane but which as no detergency of consequence. This is, however, only a speculation and there is no hard evidence to support an elucidation of the mechanism of action.

It is strongly emphasized that no particular container, collector or handling apparatus for blood samples is required to practice this invention, and that any such container, collector or apparatus may be used with and embody the present invention. Thus any blood sample container, collector or handling apparatus which comprises and effective amount of the GTPD compounds of this invention which is used to collect blood samples for use in blood assays is contemplated. For example, the conventional syringe may be prepared to collect blood and thus be within the scope of this invention by addition of the GTPD compounds to the blood sample at or very near the time of collection of the sample from the patient. Non-vacuum blood collection tubes may, likewise, be prepared and used in accordance with this invention.

Many variations of the apparatus are, of course, possible within the scope of the invention. For example, more than five percent of glycerin, EDTA, etc. may be added to give generally equivalent results but with the presence of unnecessary amounts of these reagents.

This invention is suitable for and finds its most valuable use in the sampling of the blood of patients to protect laboratory workers and others from infection during the analysis and handling of the blood sample.

INDUSTRIAL APPLICATION

This invention is useful in clinical medicine and in veterinary medicine.

What is claimed:

1. A method of analyzing blood or body fluid comprising mixing such blood or body fluid substantially at the time of sampling with one or more glycyrrhizic triterpenoid compounds in a concentration of from 0.0001 to 10.0 wt/% and from 0.0001 to 5 wt/% of one or more compounds selected from the group consisting of (a) detergent, (b) glycerol and (c) ethylene diamine tetraacetic acid or salts thereof, based on the quantity of the sample, sufficient to substantially inactivate susceptible viruses in said sample.

2. Apparatus for the sterile taking blood or other body fluid samples from patients comprising a sample collection container for such fluid containing one or more glycyrrhizic triterpenoid compounds in an amount of from 0.005 to 10 wt/% and from 0.0001 to 5 wt/% of detergent, based upon the size of the sample to be collected, said amount being effective to substantially inactivate susceptible viruses in such fluid sample.

3. A method of sampling blood or body fluid comprising mixing such blood or body fluid at the time of sampling with one or more glycyrrhizic triterpenoid compounds in a concentration of from 0.1 to 3 wt/%, and detergent in a concentration of from about 0.0001 to 5 wt/%, based on the quantity of the sample, sufficient to substantially inactivate susceptible viruses in said sample.

4. The method of claim 3 comprising the further step of maintaining the sample to which glycyrrhizic triterpenoid compound and detergent have been added at a temperature of from about 37° C. to about 60° C. for a period of up to 24 hours to assure at least a three log inactivation of virus in the sample.

5. A method of analyzing blood or body fluid comprising mixing such blood or body fluid substantially at the time of sampling with one or more glycyrrhizic triterpenoid compounds in a concentration of from 0.0001 to 10.0 wt/% and from 0.0001 to 5 wt/% of detergent based on the quantity of the sample, sufficient to substantially inactivate susceptible viruses in said sample.

6. The method of claim 6 comprising the further step of maintaining the sample to which glycyrrhizic triterpenoid compound and detergent have been added at a temperature of from about 37° C. to about 60° C. for a period of up to 24 hours to assure at least a 3-log inactivation of virus in the sample before analyzing the sample.

7. Apparatus for the sterile taking blood or other body fluid samples from patients comprising a sample collection container for such fluid containing one or more glycyrrhizic triterpenoid compounds in an amount of from 0.005 to 10 wt/% and from 0.0001 to 5 wt/% of glycerol, based upon the size of the sample to be collected, said amount being effective to substantially inactivate susceptible viruses in such fluid sample.

8. A method of sampling blood or body fluid comprising mixing such blood or body fluid at the time of sampling with one or more glycyrrhizic triterpenoid compounds in a concentration of from 0.1 to 3 wt/%, and glycerol in a concentration of from about 0.0001 to 5 wt/%, based on the quantity of the sample, sufficient to substantially inactivate susceptible viruses in said sample.

9. The method of claim 8 comprising the further step of maintaining the sample to which glycyrrhizic triterpenoid compound and glycerol have been added at a temperature of from about 37° C. to about 60° C. for a period of up to 24 hours to assure at least a three log inactivation of virus in the sample.

10. A method of analyzing blood or body fluid comprising mixing such blood or body fluid substantially at the time of sampling with one or more glycyrrhizic triterpenoid compounds in a concentration of from 0.0001 to 10.0 wt/% and from 0.0001 to 5 wt/% of glycerol based on the quantity of the sample, sufficient to substantially inactivate susceptible viruses in said sample.

11. The method of claim 10 comprising the further step of maintaining the sample to which glycyrrhizic triterpenoid compound and glycerol have been added at a temperature of from about 37° C. to about 60° C. for a period of up to 24 hours to assure at least a three log inactivation of virus in the sample before analyzing the sample.

12. Apparatus for the sterile taking blood or other body fluid samples from patients comprising a sample collection container for such fluid containing one or more glycyrrhizic triterpenoid compounds in an amount of from 0.005 to 10 wt/% and from 0.0001 to 5 wt/% of ethylene diamine tetraacetic acid or salts thereof, based upon the size of the sample to be collected, said amount being effective to substantially inactivate susceptible viruses in such fluid sample.

13. A method of sampling blood or body fluid comprising mixing such blood or body fluid at the time of sampling with one or more glycyrrhizic triterpenoid compounds in a concentration of from 0.1 to 3 wt/%, and ethylene diamine tetraacetic acid or salts thereof in a concentration of from about 0.0001 to 5 wt/%, based on the quantity of the sample, sufficient to substantially inactivate susceptible viruses in said sample.

14. The method of claim 13 comprising the further step of maintaining the sample to which glycyrrhizic triterpenoid compound and ethylene diamine tetraacetic acid or salts thereof have been added at a temperature of from about 37° C. to about 60° C. for a period of up to 24 hours to assure at least a 3-log inactivation of virus in the sample.

15. A method of analyzing blood or body fluid comprising mixing such blood or body fluid substantially at the time of sampling with one or more glycyrrhizic triterpenoid compounds in a concentration of from 0.0001 to 10.0 wt/% and from 0.0001 to 5 wt/% of ethylene diamine tetraacetic acid or salts thereof based on the quantity of the sample, sufficient to substantially inactivate susceptible viruses in said sample.

16. The method of claim 15 comprising the further step of maintaining the sample to which glycyrrhizic triterpenoid compound and ethylene diamine tetraacetic acid or salts thereof have been added at a temperature of from about 37° C. to about 60° C. for a period of up to 24 hours to assure at least a 3-log inactivation of virus in the sample before analyzing the sample.

17. Apparatus for the sterile taking blood or other body fluid samples from patients comprising a sample collection container for such fluid containing one or more glycyrrhizic triterpenoid compounds in an amount of from 0.005 to 10 wt/% and from 0.0001 to 5 wt/% of one or more compounds of the group consisting of (a) detergent, (b) glycerol, and (c) ethylene diamine tetraacetic acid and salts thereof, based upon the size of the sample to be collected, said amount being effective to substantially inactivate susceptible viruses in such fluid sample.

* * * * *